(12) United States Patent
Sanders, Jr.

(10) Patent No.: US 6,762,193 B1
(45) Date of Patent: Jul. 13, 2004

(54) METHOD OF TREATING HAIR LOSS

(76) Inventor: Richard J. Sanders, Jr., 77173 Highway 21, Covington, LA (US) 70453

( * ) Notice: Subject to any disclaimer, the term of this patent is extended or adjusted under 35 U.S.C. 154(b) by 57 days.

(21) Appl. No.: 10/228,508

(22) Filed: Aug. 27, 2002

Related U.S. Application Data

(62) Division of application No. 09/821,775, filed on Mar. 29, 2001, now Pat. No. 6,440,994.
(60) Provisional application No. 60/193,030, filed on Mar. 29, 2000.

(51) Int. Cl.[7] .................. A61K 31/47; A61K 31/405
(52) U.S. Cl. ................................ 514/311; 514/415
(58) Field of Search ............................... 514/311, 415

(56) References Cited

U.S. PATENT DOCUMENTS

| | | | | |
|---|---|---|---|---|
| 5,248,685 A | * | 9/1993 | Eggler et al. | 514/311 |
| 5,384,218 A | * | 1/1995 | Tokui et al. | 430/5 |
| 5,466,669 A | * | 11/1995 | Konig et al. | 514/12 |
| 5,698,550 A | * | 12/1997 | Eggler et al. | 514/217.04 |
| 5,908,858 A | * | 6/1999 | Kimura et al. | 514/427 |
| 5,952,326 A | * | 9/1999 | Eggler et al. | 514/213.01 |
| 5,998,451 A | * | 12/1999 | Eggler et al. | 514/367 |
| 6,166,031 A | * | 12/2000 | Eggler et al. | 514/311 |
| 6,451,801 B1 | * | 9/2002 | Scannell et al. | 514/253.03 |

* cited by examiner

*Primary Examiner*—Vickie Kim
(74) *Attorney, Agent, or Firm*—Garvey, Smith, Nehrbass & Doody, L.L.C.; Seth M. Nehrbass

(57) ABSTRACT

A method of treating inflammatory skin diseases and/or hair loss, comprising administering to a patient in need of such treatment a therapeutically effective amount of a leukotriene receptor anatagonist, an antihistamine, or other anti-inflammatory drug, preferably at least twice a day, preferably for at least two months.

8 Claims, No Drawings

METHOD OF TREATING HAIR LOSS

CROSS-REFERENCE TO RELATED APPLICATIONS

This application is a division of application Ser. No. 09/821,775, filed Mar. 29, 2001, now U.S. Pat. No. 6,440,994. Priority of my U.S. Provisional Patent Application Serial No. 60/193,030, filed 29 Mar. 2000, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to acne and other inflammatory skin diseases. More particularly, the present invention relates to methods of treating acne and other inflammatory skin diseases including, but are not limited to, acne vulgaris, acne rosacea, acne conglobata, sebaceous cysts and hidrandenitis suppurativa through the oral administration of at least one drug selected from the group consisting of anti-leukotriene agents, and anti-histamine agents. These include, but not limited to, leukotriene antagonists, blockers, and inhibitors as well as histamine antagonists, blockers, and inhibitors.

2. General Background of the Invention

Acne vulgaris is a dermatological disorder that affects 17 million Americans with a prevalence rate exceeding 85% in teenagers, declining to about 8% in 25 to 34 year olds, and to 3% in 35 to 44 year olds[8]. It is multifactorial and its course varies with cause and age. "There is no disease that produces more psychic trauma, maladjustment, insecurity, and feelings of inferiority than does acne."[13]

For many family physicians acne vulgaris is a very complex and challenging illness due to its inconsistent and often mutable response to treatment. All too many physicians are aware of the insidious nature of this disease and the intense emotional or physical disturbance resulting from acne. No other malady has as its consequence such intense feelings of inferiority, maladjustment and insecurity. The majority of cases seen in the outpatient clinical arena are those that have either been previous treatment failures or those that are presenting for re-treatment because of ongoing medical noncompliance. Often patients are disinclined to continue a chronic, multidrug treatment regimen because of the potential for developing undesirable side effects, notwithstanding, the assumption of burdensome medical risks; Avoidance of treatment measures usually results in predictable exacerbations of acne lesions and a depreciative outcome, whereas treatment tolerance and potential adversity is rewarded with success.

Recently several authors have reviewed and summarized the treatment options for acne vulgaris.[8, 10] Although effective treatment is available for both short and long term management of acne vulgaris, a strategy for oversight and individualization is essential as relapse is not uncommon; nonetheless, satisfactory results are not guaranteed with the use of any one of the currently available drugs alone. Although the medical causes of acne vulgaris are not known, most patients can be managed with a variety of drugs that have been developed recently. However, results vary based on one's particular choice of chemotherapy or method of medical management Although many effective pharmaceutical preparations, both prescription and nonprescription, are currently available for use in the treatment of acne vulgaris, no one drug appears effective against all distinctive types of acne and most preparations are laden with significant side effects. Comedolytic agents, for example, in their attempt to promote comedonal drainage cause significant skin irritation. Topical antibiotics decrease the number of mild to moderate inflammatory lesions by inhibiting the growth of p. acnes and are also associated with skin irritation, dryness, and potential antibiotic resistance. Oral antibiotics are the standard for treating moderate to severe acne lesions, however, superinfection may occur and long-term use requires routine laboratory monitoring. Hormones in their attempt to decrease sebum production are not without side effects and are usually reserved for females. Oral Vitamin A acid derivatives, although very effective, are only approved for severe nodular acne and commonly exhibit serious adverse reactions.[8]

Anti-infectious agents, have also been used as a treatment for acne and other inflammatory skin diseases. Although used quite often in family practice and other medical settings, anti-infectious agents at doses effective for other diseases do not completely eradicate acne within a reasonable period of time. Even at the higher doses of anti-infectious chemotherapy used for more aggressive diseaes, these anti-infectious agents do not completely clear acne.

I note here Mat acne appears to be more inflammatory than infectious, inflaming the face surround the pilosebaceous unit and only "infecting" a single pilosebaceous unit Acne is not characterized by a classic cellulitis that would assume to be migrating from the microabscess region Rather, it develops a perilesional inflammatory reaction that persists and remains insidious until medical intervention occurs. If acne were indeed an "infectious" disease, left untreated we would expect it to spread to contiguous tissue creating a substantial problem. However, it never appears to do so.

In addition, the currently available treatments and management of acne and other inflammatory skin diseases using antibiotics appears to violate basic medical principles. Acne is a characterized as a microabscess. An abscess is typically treated by incision and drainage, not by antibiotics. Propionibacterium acnes (p. acnes) is an anaerobic diptheroid organism that does not appear to cause disease in any other areas of the human body. Thus, P. acnes should not be perceived as a primary pathogen but rather as an opportunist that becomes entrapped in the pilosebaceous unit. When entrapped, an anaerobic environment is created. This allows the bacteria to multiply, and pustie to form which eventually causes an inflammatory response in the individual. Certainly, when this occurs antibiotic treatment is useful to remove the growing bacteria and accounts for some of the limited success seen in patients treated with antibiotics.

What is needed is a treatment that is effective against all distinctive types of acne and a variety of other inflammatory skin diseaes and is not laden with significant side effects.

Since the mid 1970's medical research has emphasized and shown substantial evidence that a temporary excessive dihydrotestosterone production is implicated in the pathogenesis of acne vulgaris, androgenetic alopecia, idiopathic hirsutism and benign prostatic hypertrophy[7]. The studies by Sansoni and Mauvais-Jarvis clearly associate a local increase in dihydrotestosterone formation with the development of acne,[7] and skin functions such as sebum secretions (Strauss and Pochi, 1963) and body hair growth are well known to be under androgen control[4]. The special article by Price in 1975 suggests that with the proper antiandrogen the highly desirable effect of reducing excessive dihydrotestosterone formation by blocking or selectively inhibiting testosterone 5 alpha reduction should have little systemic effect and the psychological and other important roles of testosterone itself should not be affected[7]. Nonetheless, current therapy utilizing pharmacological agents that exhibit antiandrogenic activity have failed to live up to earlier expectations in the management of these diseases. For instance, the Type II 5 alpha reductase specific inhibitor Finasteride (Propecia), indicated for the treatment of androgenetic alopecia in men, is contraindicated in women and children and is associated with considerable precautions and adverse reactions such as two fold elevations in serum prostatic specific antigen and decreased labido, erectile dysfunction and ejaculatory dysfunction respectively[6].

The following U.S. Patents are incorporated herein by reference: U.S. Pat. No. 6,034,228 Human signal transduction serine/threonine kinase, U.S. Pat. No. 6,034,057 Peptide inhibitors of fibronectin, U.S. Pat. No. 6,034,056 Fibronectin adhesion inhibitors, U.S. Pat. No. 6,008,223 Therapeutic compounds, U.S. Pat. No. 5,998,444 Piperidinyl compounds as NK1 or NK2 antagonists, U.S. Pat. No. 5,993,859 Pharmaceutical agents, U.S. Pat. No. 5,990,130. Therapeutic heterocycles, U.S. Pat. No. 5,977,135 Bicyclic heterocycles, U.S. Pat. No. 5,965,576 Cyclic amide derivatives for treating asthma, U.S. Pat. No. 5,965,396 Human lymph node derived GTPase, U.S. Pat. No. 5,962,265 Human signal transduction serine/threonine kinase, U.S. Pat. No. 5,900,432 Therapeutic N-(4-benzoyl-2-methyl-phenyl)-3,3,3-trifluoro-2-hydroxy-2-methyl-propanamides, U.S. Pat. No. 5,889,024 Substituted heterocycles, U.S. Pat. No. 5,866,568 Heterocyclic compounds, U.S. Pat. No. 5,861,401 N-heterocyclyl sulphonamide derivatives and their use as endothelin antagonists, U.S. Pat. No. 5,861,392 Therapeutic heterocycles, U.S. Pat. No. 5,739,149 Substituted piperidinobutyl nitrogen-containing hetercyclic compounds and analogues thereof as neurokinin antagonists, U.S. Pat. No. 5,731,309 Substituted heteroalkyleneamine neurokinin antagonists, U.S. Pat. No. 5,710,169 Therapeutic heterocycles, U.S. Pat. No. 5,705,505 Cyclic amide derivatives for treating asthma, U.S. Pat. No. 5,700,798 Methods for using benzoxazines for treating asthma, U.S. Pat. No. 5,693,639 Therapeutic heterocyclyl amionosulfonyl phenyl compounds, U.S. Pat. No. 5,677,317 Lactam compounds which are useful in the treatment of asthma, U.S. Pat. No. 5,668,137 N-heterocyclic sulfonamides having endothelin receptor activity, U.S. Pat. No. 5,654,299 Aryl substituted heterocycles, U.S. Pat. No. 5,641,793 Pyridine compounds which have useful pharmaceutical activity, U.S. Pat. No. 5,635,509 Piperidine derivatives useful as neurokinin antagonists, U.S. Pat. No. 5,622,964 Heterocyclic derivatives, U.S. Pat. No. 5,612,367 Method of enhancing bioavailability of pharmaceutical agents, U.S. Pat. No. 5,602,138 NKA affecting piperidyl heterobicyclic compounds, U.S. Pat. No. 5,589,489 Cyclic amide derivatives for treating asthma, U.S. Patent No. 5,583,152 Method for treating vasospastic cardiovascular diseases heterocyclic amide derivatives, U.S. Pat. No. 5,576,333 Carboxamide derivatives, U.S. Pat. No. 5,567,700 Therapeutic heterocycles which antagonize neurokinin receptors, U.S. Pat. No. 5,559,132 Carboxamide derivatives for treating asthma, U.S. Pat. No. 5,559,131 Carboxamide derivatives for treating asthma, U.S. Pat. No. 5,534,525 Lactam derivatives; U.S. Pat. No. 5,521,199 Piperidinyl compounds as neurokinin receptor antagonists, U.S. Pat. No. 5,512,594 Ether derivatives having 5-lipoxygenase inhibitory activity, U.S. Pat. No. 5,510,386 Aminosulfonylphenyl compounds for treating urinary incontinence, U.S. Patent No. 5,504,216 Method for repairing an amorphous sulfonamide, U.S. Pat. No. 5,504,089 2-hydroxyalkyl-benzimidazoles, - quinazolines and -benzothiawles as potassium channel agonists, U.S. Pat. No. 5,486,515 2-fluoroalkyl-1,4-benzoxaxines as potassium channel mediators, U.S. Pat. No. 5,482,969 Certain N(4-benzoyl-2-phenyl)-3-trifluoro-2-hydroxy-propananude derivatives, U.S. Pat. No. 5,482,966 Oxime derivatives, U.S. Pat. No. 5,482,963 Phanmaceutical agents useful as leukotriene antagonists, U.S. Pat. No. 5,478,843 Thiazole derivatives, U.S. Pat. No. 5,478,842 Ether derivatives having 5-lipoxygenase inhibitory activity, U.S. Pat. No. 5,457,125 Oxime derivatives, U.S. Patent No. 5,455,253 Heterocyclic derivatives. U.S. Pat. No. 5,453,439 Hydroxylamine derivatives, U.S. Pat. No. 5,440,035 Heterocyclic amide derivatives, U.S. Pat. No. 5,420,298 Pyrrolidine derivatives, U.S. Pat. No. 5,411,973 Therapeutic alcohols, U.S. Patent No. 5,401,751 Isoquinoline derivatives suitable for use in leukotriene mediated disease, U.S. Pat. No. 5,391,758 Heterocyclic amide derivatives, U.S. Pat. No. 5,376,680 Oxime derivatives, U.S. Pat. No. 5,373,007 Pyridooxazinyl or pyridothiazinyl as inhibitors of leukotrienes, U.S. Pat. No. 5,367,079 Cycloalkane derivatives, U.S. Pat. No. 5,350,754 Heterocyclic cycloalkanes, U.S. Pat. No. 5,338,734 Heterocyclic amide derivatives and pharmaceutical use thereof, U.S. Pat. No. 5,334,614 Hydroxylamine derivatives, U.S. Pat. No. 5,332,757 Oxime derivatives.

BRIEF SUMMARY OF THE INVENTION

A method of treating acne and other inflammatory skin diseases is provided which comprises administering to a patient in need of treatment an anti-leukotriene or antihistamine agent, or other anti-inflammatory agent alone or in combination, preferably twice a day, preferably for at least two months.

DETAILED DESCRIPTION OF THE INVENTION

Current treatment outcomes in patients with acne vulgaris are not consistent nor fully explained with present day therapy. Immunological factors appear to play a more important role than previously recognized. Because acne is an inflammatory skin disease, we investigated the use of anti-inflammatory agents on the treatment of acne. The anti-inflammatory agent we investigated most fully included the anti-leukotriene, zafirlukast.

With the onset of puberty and under the direction of androgenic hormones sebaceous glands enlarge secondary to increased triglyceride formation. Triglycerides are then hydrolyzed to free fatty acids by the enzyme hyaluronidase from *p. acnes*. With the release of hyaluronidase by *p. acnes*, hyaluronic acid present in cell coats breaks down. Free fatty acids are not truly immunogenic by themselves but become so by virtue of their chemical reactivity with self skin proteins thereby creating larger conjugates.[4] Increasing complexity as well as host genetic factors contribute to a molecules immunogenicity. In the presence of this free fatty acid moiety, or immunogen, cell surface antibodies or immune system cells become reactive, triggering the release of leukotrienes, histamines, and other vasoactive substances. Tissue congestion occurs compromising the orifice of the pilosebaceous complex ultimately creating an impaction at the follicle. The microcomedo, or acne precursor lesion, is the resultant product of this process. Extravasation of the contents of the pilosebaceous unit into the surrounding dermis results in the inflammatory acne lesion. Eventually, follicle walls rupture and acne nodules develop. Supportation of the acne nodule results in the acne cyst.

Because the inflammatory response of the acne lesion is mediated by the release of leukotrienes, and histamines, then the introduction of anti-leukotrienes and/or antihistamines will effectively prevent the formation of new acne lesions and exert a significant impact on the resolution of old lesions.

Anti-leukotrienes are a topic of great interest at the present time. Leukotriene (LT) synthesis begins with phospholipase $A_2$ mediated conversion of phosphatidyl choline from the nuclear membrane to arachidonic acid. Arachidonic acid binds to 5-lipoxygenase (5-LO) activating protein (FLAP) effectively increasing its concentration in the vicinity of the 5-LO enzyme. Arachidonic acid is then converted to leukotriene $A_4$ ($LTA_4$). $LTA_4$ may then be converted to the chemotaxin $LTB_4$, or, in sequential steps to $LTC_4$, $LTD_4$, and $LTE_4$. $LTC_4$, $LTD_4$, and $LTE_4$ are the cysteinyl leukotrienes.

There are two types of anti-leukotriene agents, LT synthesis inhibitors and LT receptor antagonists. Zafirlukast is an anti-leukotriene that competitively inhibits the binding of leukotriene D4 at its receptor site. Currently, the medical applications of zafirlukast is in the prophylactic treatment of patients with mild to moderate asthma.[5] Zafirlukast alone has already become established as the standard of care in long term asthma management in both adolescence and adults, and is now indicated for use in the pediatric population aged seven and above. Results of other studies suggest efficacy in the treatment of leprosy reaction,[14] migraine prophylaxis[11], atopic dermatitis[2] and chronic urticaria.[12]

It is important to note that zafirlukast (such as Accolate®) is a selective and competitive receptor antagonist of leukotriene $D_4$ and $E_4$ components of slow reactive substances of anaphylaxis. Zafirlukast is a member of a class of drugs initially called the $LTD_4$-receptor-antagonists. These drugs are now named the $CysLT_1$-antagonists to "recognize that each of $LTC_4$, $LTD_4$ or $LTE_4$ is a potential natural agonist at their common receptor in human airways"[9]. Zafirlukast inhibits leukotriene formation by competitively inhibiting the binding of leukotriene $D_4$ at its receptor site; it does not inhibit the formation of leukotriene $B_4$ Because leukotriene $B_4$ is relatively high up in the cascade of events leading to the synthesis of the cysteinyl leukotrienes ($LTC_4$, $LTD_4$, and $LTE_{,4}$), blocking leukotriene $B_4$ formation can cause more general and significant deleterious side effects not seen by more specific targeting of the downstream leukotrienes $LTC_4$, $LTD_4$, and $LTE_4$ as is the case with zafirlukast

EXAMPLE #1

This study was designed to evaluate the effectiveness in treating acne vulgaris with the drug zafirlukast After having established a mechanism by which zafirlukast would be effective in the treatment of acne vulgaris, and subsequently treating a single case of acne conglobata successfully during the summer and fall of 1999, this study was purposely designed to evaluate the treatment of acne vulgaris with the drug zafirlukast Objective: To determine if the anti-leukotriene zafirlukast is effective in the treatment of acne vulgaris/acne rosacea.

Design: Inception cohort investigational study conducted from October 1999 to January 2000.

Setting: Rural Family Practice clinic in Waldheim, La.

Participants: A total of 7 male and 8 female patients aged 12–45 years diagnosed with mild, moderate, or severe acne vulgaris including one case of acne conglobata and 2 cases of acne rosacea were given 20 mg. of zafirlukast (ACCOLATE® brand from AstraZeneca) twice daily from week 1 through week 4. The dose was increased to 30 mg. twice daily at week 4 and continued through week 8. At week 8 the dose of zafirlukast was decreased to 20 mg twice daily and continued until the termination of the study at 10 weeks.

Between the months of October and November 1999 both adolescent and adult patients were recruited consecutively at a family practice clinic in rural Louisiana to participate in an investigational study to determine the effectiveness of zafirlukast in the treatment of acne vulgarism Those patients who provided informed consent and who have reported a prior medical diagnosis of acne vulgaris were enlisted into the study. This cohort was composed of a total of seven male and eight female Caucasian patients, age twelve to forty five years, diagnosed with mild, moderate or severe acne vulgaris.

Pre-study recruitment assessment data was consistent with the following: one of fifteen patients was diagnosed with acne conglobata; two of fifteen patients were diffused with acne rosacea, one of which had acne scars who had previously been treated with oral isotretinoin for nodular-cystic acne; eleven of fifteen patients with moderate to severe inflammatory/nodular-cystic acne; all patients had self medicated with topical comedolytic over-the-counter agents; three of fifteen patients had never been treated with prescription (topical or systemic) medications; twelve of fifteen patients were prescribed a range of three to five medical prescriptions (both topical and systemic) with varying degrees of success and failure; three of fifteen patients had previously taken oral isotretinoin; two of fifteen patients had been offered oral isotretinoin but refused that treatment.

Inclusion criteria for study enlistment encompassed any patient who was requesting medical treatment of a chief complaint of acne dermatitis, coincident with a clinical diagnosis of acne vulgaris confirmed by physical examination. These patients voluntarily agreed to be treated with zafirlukast knowing that alternative treatment (both topical and systemic) were available. At the initial visit all patients were instructed on the use of zafirlukast This was to be administered by mouth twice daily. The potential side effects, potential adverse reactions, and other risks were all explained. Patients all agreed to avoid any over-the-counter acne preparations and were to use any household soft-soap product to wash the facial skin twice daily. Zafirlukast was to be administered at the dose of 20 mg. twice daily from week one through week four and then to be increased to 30 mg. twice daily at week four and continued through week eight. At week eight the dose of zafirlukast was to be decreased to 20 mg. taken twice daily and continued until the completion of the study at ten weeks.

Main Outcome Measures: Subjective and objective medical examination and qualitative photographic analysis were employed at each patients initial visit to establish baseline. Thereafter, each patient was consecutively examined and photographed at two to three week intervals. At each respective visit, treatment benefits were assessed, compliance was questioned, and side effects, if any, noted. Patient satisfaction was measured by having all participants complete a post study survey. This questionnaire allowed patients to document adversities or side effects, self-esteem improvement, diminution of facial pain and discomfort, and overall satisfaction with the course of treatment. Data was utilized from primary care visits at the Waldheim Family Practice Clinic.

Results: All fifteen patients finished the study and completed the post study survey. Significantly, all participants attained periods of acne remission during the study. Subjective and objective clinical improvement was observed as early as two weeks, but routinely occurred within 3–4 weeks of initiating zafirlukast therapy. All cases of mild, moderate, or severe acne vulgaris studied including acne rosacea, acne conglobata, and nodulocystic acne responded similarly in their observed periods of remissions or exacerbations. The data were correlated with qualitative photographic analysis. Satisfaction ratings in the post study survey were high and most patients preferred to continue zafirlukast alone or as combination therapy with other comedolytic or anti-infective agents.

In so much as there was a continual decline in both inflammatory and non-inflammatory acne lesions during this study, patient self-esteem progressed and appeared to improve by week four, and matured by week eight, only falling off slightly during periods of acne recurrence. Remission of acne vulgaris, characterized by the absence of new lesion formation, old lesion regression and the observed decline in perilesional erythema and facial discomfort, were all factors contributing to the amelioration of patient self-esteem.

Only one patient was compliant in taking zafirlukast throughout the entire study. He was able to maintain complete remission and accomplish total regression of any inflammatory acne lesion. He experienced only a mild facial erythema for two days following the dosage drop from 30 mg to 20 mg.

However, it was not uncommon for patients to miss anywhere from two to three consecutive doses in any one week and six patients had significant dosage discontinuation each at nine, seven, six, five, and two at three consecutive days, respectively. One patient who missed three consecutive days also missed every weekend throughout the entire study. Only one person requested referral to dermatology at the termination of the study. Data analysis revealed that he was one of two participants consistently non-compliant throughout the entire study. It should be noted, however, that medical noncompliance is not a quite uncommon finding during the management of a chronic medical condition during any study and does not reflect the success of the treatment. For example, in this study, factors that contributed to non-compliance include the twice daily dosing requirements, a false sense of well being once remission was realized, the mere fact that most patients whom were non compliant were in the study group compromising those in the teenage years and usually took weekend a retreat from their homes and the guidance of their parents whom were directing their therapy to some degree. There were also those who were content with the remission of new lesions and less inclined to be concerned with the regression of old acne lesions.

Those who were consistently non-compliant had acne reoccurrence within 2–3 days after more than 2–3 doses missed. Discontinuation of zafirlukast therapy over a 5–7 day period was associated with reoccurrence of acne form lesions equal to baseline levels. However, reinstitution of zafirlukast therapy was associated with old lesion regression and new lesion remission, commonly occurring within a period of time resembling the duration of zafirlukast deprivation. There appeared to be no added benefit observed in taking 30 mg. twice daily from week 4 thru week 8.

Although perilesional erythema appeared to resolve only by approximately 10–15% by week two, significant reductions of 40–50% and 80–90% were achieved by weeks four and eight respectively. Remarkably, there was little if any perilesional erythema accompanying the development of any new inflammatory acne lesion that developed while any patient was taking zafirlukast.

One participant who suffered with acne rosacea felt a sense of asthenia in taking zafirlukast on an empty stomach, thereafter she continued the study from week two through, week ten at 10 mg. dosage levels twice daily with no further side effects observed. She was the only participant whom ever realized any potential side effects while being treated with zafirlukast.

Conclusion: This study substantiates efficacy in modifying the inflammatory reaction of acne vulgaris Zafirlukast exerts a potent therapeutic effect on the acne process and plays a pivotal role in the prophylactic management of acne vulgaris. The recommended dosage of zafirlukast for adults ($\geq 12$ years) is 20 mg twice daily; for pediatrics (7–11 years) the recommended dosage is 10 mg twice daily. The preferred daily dosage range of zafirlukast for adults (>12 years) is about 20 mg twice daily; for pediatrics (7–11 years) the recommended dosage is about 10 mg twice daily. It is preferably taken twice daily or administered in a form that it is released into the bloodstream twice daily. It is preferably taken consistently for at least 4 weeks, more preferably at least 8 weeks, and even more preferably at least 12 weeks. Most preferably, it is taken every day without stopping. The method of the present invention is most effective if zafirlukast is taken as prescribed every day. Additional controlled studies, such as double blind placebo studies, increasing drug dosage at the onset and throughout entire length of study, prolonged study periods and study protocols that would include anti-leukotriene therapy side by side with comedolytic anti-infective, anti-histamine and anti-androgen therapies will demonstrate the significant value of zafirlukast in patients who suffer from this dreadful disease.

Other Effective Treatments Encompassed by the Present Invention

In addition to zafirlukast, the following drugs will also be effective in treating acne and other inflammatory skin diseases.

Montelukast (such as Singulair®) is another leukotriene blocker. Singulair was tested and shown to be effective. It is a selective and orally active leukotriene receptor antagonist that inhibits the cysteinyl leukotriene receptor. The recommended dosage for adults ($\geq 15$ years) is 10 mg in the evening; for pediatrics (6–14 years) the recommended dosage is 5 mg in the evening.

Leukotriene inhibitors (such as cromolyn sodium) will also work, but may be less desirable as they may have harmful side effects. Cromolyn sodium acts by inhibiting the release of histamine and leukotrienes from the mast cell. In vitro and in vivo animal studies show that cromolyn sodium inhibits synthesized mast cell degranulation that occurs after exposure to specific antigens. Cromolyn sodium acts by inhibiting the release of mediators from mast cells. Studies show that cromolyn sodium directly blocks calcium ions from entering the mast cell thereby preventing mediator release. Cromolyn sodium inhibits both the immediate and non-immediate bronchoconstrictor reactions to inhaled antigens. Cromolyn sodiun also attenuates bronchospasm caused by exercise, aspirin, cold air, sulfur dioxide and environmental pollutants (see Physicians' Desk Reference page 987, 50th edition 1966).

Examples of commercially available cromolyn sodium are Gastrocrom®, Intal inhaler®, Intal nebulizer solution, Opticrom Ophthalmic solution and cromolyn sodium inhalation solution USP. The recommended dosage of Gastrocrom® for adults (13+) is two 100 mg ampoules taken orally 4 times per day (800 mg daily total), ½ hour before meals and at bedtime, and for children 2–12, one 100 mg ampoule taken orally 4 times per day (400 mg daily total), ½ hour before meals and at bedtime.

Zileuton (such as Zyflo®) is an oral active inhibitor of 5-lipoxygenase, the enzyme that catalyzes the formation of leukotriene from arachidonic acid. The recommended dosage for adults ($\geq$18 years) is 600 mg four times per day (2400 mg daily total).

Histamines play some role in acne formation, and antihistamines administered daily will help reduce acne formation. Preferred antihistamines include loratadine (e.g. Claritin®), ranitidine (e.g. Zantac®), cimetidine (e.g. Tagamet®), famotidine (e.g. Pepsid®), nizatidine (e.g. Axid®), and fexofenadine (e.g. Allegra®), hydroxyzine HCl (e.g. Atarax), cyprohepadine (e.g Periactin), promethazine HCl (e.g. Phenegan), cetrizine (e.g. Zyrtec), and hydroxyzine pamoate (e.g. Vistaril) because they do not sedate. However, other antihistamines would work as well. It is believed that antihistamines administered daily may help reduce acne formation if taken for 2 months or longer.

Loratadine is especially preferred due to its dual action of acting as an antihistamine and as a leukotriene C4 antagonist Examples of Antihistamines Useful in the Present Invention:

A. Histamine $H_1$-receptor antagonist compounds that can be used in the method of the present invention include those listed in the Physicians Desk Reference (2000 ed.) under the following product categories in the blue pages on page 204, etc.: 1) antihistamines and combinations; 2) also see under nasal preparations—antihistamines; and 3) ophthalmic preparations—antihistamines and combinations.

B. Histamine $H_1$-receptor antagonist compounds that can be used in the method of the present invention include those corresponding to the ones listed in A above which are listed in the nonprescription P.D.R. (2000 ed.).

C. Histamine $H_2$-receptor antagonist compounds that can be used in the method of the present invention include those listed in the Physicians Desk Reference (2000 ed.) on page 210.

D. Histamine $H_2$-receptor antagonist compounds that can be used in the method of the present invention include those corresponding to the ones listed in C above which are listed in the nonprescription Physicians Desk Reference (2000 ed.).

The method of the present invention will also work for sebaceous cysts as well as acne.

If no dosages are listed herein for a particular drug, the dosage recommended for treatment of asthma can be used.

Hair Loss Treatment Method

INTRODUCTION

The significance of inflammation in acne pathogenesis is well described in the literature over the past several decades. In as much as it has been clinically proven that the inflammatory reaction associated with acne vulgaris, and rosacea resolves in patients taking zafirlukast, which competitively antagonizes the cellular receptor for cysteinyl leukotrienes, the cyst LT 1 receptor[7]., there is still no adequate explanation as to why patients suffering from these dreaded diseases develop a state of remission while taking this drug. Having considered the research data presented thus far, several questions still remain. Considering the fact that acne vulgaris is androgen mediated, does zafirlukast exhibit antiandrogen activity, and if so, would this drug have any benefit in treating other diseases know to be mediated by antrogens? In an attempt to answers these questions, further study was undertaken to determine whether or not a biological marker exists that would explain our findings and if so would current and past scientific investigation support our conclusion.

DISCUSSION

STUDY

During the summer of 2000 an investigative study was initiated to determine the efficacy of zafirlukast in the treatment of androgenetic alopecia A middle aged 40 year old blond haired caucasian male whom was actively undergoing genetically influenced alopecia was recruited and voluntarily enlisted into the study under informed consent. Prior to taking zafirlukast this patient had never received treatment for androgenetic alopecia and physical examination showed no evidence of pathological hair loss. Zafirlukast was initiated at a dose of 20 mg taken twice daily and within the first 6 weeks of zafirlukast treatment both the patient and his wife witnessed less occurrence of hair loss and by the fourth month of treatment regrowth of hair in the area of temporat and vertex balding was observed. Serum ancillary studies obtained at the completion of his fourth month of zafirlukast therapy revealed a dihydrotestosterone level of 32 NG/DL (normal 25 to 75 NG/DL). Just two months earlier serum luteinizing hormone, total testosterone, androstenedione and dehydroepiandrosterone sulfate levels were determined to be normal. Having considered that dihydrotestosterone levels may have been suppressed to a low normal range, as pre treatment dihydrotestosterone serum determination had not been performed, the dose of zafirlukast was increased to 40 mg taken by mouth twice daily. Continuing this dose for a one month period of time, serum dihydrotestosterone levels were reanalized and determined to be 21 NG/DL (normal 25 to 75 NG/DL). Additionally, serum 3-alpha androstanediol glucuronide, estrone, androstenedione, total testosterone, prostate specific antigen, and progesterone levels were within normal limits at this time. The patient was then withdrawn, from zafirlukast therapy and there were no specific complications or side effects during a one month abstinence from zafirlukast and serum dihydrotestosterone levels were redetermined and found to be 15 NG/DL (normal 25 to 75 NG/DL). This patient was then given the option to continue treatment with zafirlukast at a dose of 40 mg taken by mouth twice daily for the treatment of androgenic alopecia and decided to do so as he had witnessed the continued regrowth of hair and remission of hair loss while taking zafirlukast. There were never any side effects observed while he was taking zafirlukast In an attempt to verify and cross reference these significant findings with a male patient undergoing treatment with zafirlukast for acne vulgaris and a female patient whom enlisted into a study to determine the effects of zafirlukast on hereditary balding and whom had previous treatment failures with finasteride, blood serum analysis was performed to determine whether or not dihydrotestosterone suppression was also occurring in these individuals as well.

The results are as follows:

In a 19 year white male undergoing treatment for Grade IV cystic acne vulgaris with zafirlukast at 40 mg po bid (by mouth twice a day) for 4 weeks, preceded by 2 weeks of zafirlukast treatment at 30 mg bid, his serum dihydrotestosterone level was determined to be 16 NG/DL (normal was 25 to 75 NG/DL).

In a 53 year old white female undergoing treatment with zafirlukast at 40 mg po bid for hereditary balding, her pretreatment dihydrotestosterone level was 5 NG/DL (normal 5 to 30 NG/DL); after 4 weeks of continuous treatment her dihydrotestosterone serum concentration was 4 NG/DL (normal 5 to 30 NG/DL) and at 6 weeks of continued treatment her serum dihydrotestosterone level was determined to be less than 3 NG/DL.

In both of these individuals not only was dihydrotestosterone suppression realized but a significant improvement in acne lesion remission and clearing in the male individual and regrowth of frontal hair in the female individual was documented. Both individuals continued medical treatment and management of their respective illnesses under informed consent never witnessing any side effects or adversities and are pleased with their outcomes thus far.

DISCUSSION

For many years medical researchers have studied the pathways of androgen metabolism and have recognized its undesirable consequences i.e., acne vulgaris, androgenetic alopecia, idiopathic hirsutism and benign prostatic hypertrophy, besides others. There now appears to be significant evidence to suggest that in some individuals the drug zafirlukast not only blocks the potent inflammatory reaction mediated by leukotrienes, but also possess antiandrogen activity as well.

In this study a dose and time dependent effect has been identified with the treatment of both acne vulgaris and common baldness in genetically susceptible men and women without physical or psychological compromise, or forfeit of quality of life. The use of zafirlukast in treating these dreaded diseases appears to be safe and effective at doses above those recommended for the treatment of asthma as shown in this study. Serum liver function studies monitored during this study remained in the normal range of value except in one patient with known Hepatitis C and abnormal pretreatment liver function studies; however, in all patients including the one patient with Hepatitis C, serum liver function studies improved with zafirlukast treatment possibly indicating a role in treating liver diseases in the future.

There are several biological mechanisms that could be implicated in explaining the results of this study including the following:

A) By inhibiting the action of 5-alpha reductase or 17 beta-hydroxysteroid dehydrogenase, the two principal pathways of testosterone metabolism in all growing hairs and skin cells[7].

B) By inhibiting the formation or action of the metabolite of testosterone or androstenedione i.e. dihydrotestosterone, 5-alpha androstanediol, 5-alpha androstanedione, 5-alpha androsterone or estrone[7].

C) By inhibiting the peripheral conversion of androstenedione to testosterone in the skin[7].

D) By inhibiting adenyl cyclase due in fact to high dihydrotestosterone levels in the hair follicle(high dihydrotestosterone levels in genetically marked hair follicles initiate baldness by inhibiting adenyl cyclase)[7].

E) By alteration of the androgen receptor protein in the peripheral target cells allowing them to concentrate androgens at the presumed site of action in the cell nucleus i.e., interception, antagonism, or inhibition of the highly specific antrogen receptor protein that binds with dihydrotestosterone and transports it to the cell nucleus[7].

F) By blocking dihydrotestosterone at a given target site[7].

G) By promoting the formation of progesterone[7].

H) By promoting the formation of steroids all having structural resemblance to testosterone and thus competing with testosterone for the binding site on the enzyme 5-alpha reductase i.e., 4 androsten-3-one-17 beta-carboxylic acid, androstenedione and deoxycorticosterone[7].

CONCLUSION

Zafirlukast is both safe and effective in the treatment and management of inflammatory and androgen mediated disorders for which dihydrotestosterone suppression and leukotriene antagonism is desired. Although more rapid and sustained effects are produced at elevated dosage levels, adequate disease resolution occurs at doses not associated with serum dihydrotestosterone suppression below the lower limits of normal relative to one's age or sex, suggesting that a dual mechanism of action exist for zafirlukast i.e., antileukotriene and antiantrogen effects. This new found idea and discovery will help strengthen our understanding of treating acne vulgaris, androgenic alopecia, female hereditary balding and other androgen or leukotriene mediated illnesses and in fact may change our way of thinking and approach to these significant illnesses whose symptoms and disease characteristics are ameliorated with the use of zafirlukast. Additional research and development of the drug zafirlukast is recommended at this time.

All measurements disclosed herein are at standard temperature and pressure, at sea level on Earth, unless indicated otherwise. All materials used or intended for use in a human being are biocompatible, unless indicated otherwise.

The foregoing embodiments are presented by way of example only; the scope of the present invention is to be limited only by the following claims.

References

1. Antileukotriene working group: Left A R, Spector S L, Strek M, et al. The role of Antileukotriene Agents in Clinical Practice. Asthma 2000 Monograph Series, Oct. 31, 1999, Zeneca Pharmaceuticals; Concensus Statement; 1–16.
2. Carucci J A, Washenik K, Weinstein A. et al, The Leukotriene Antagonist Zafirlukast as a Therapeutic Agent for Atopic Dermatitis. Arch. Dermatol. 1998; 1134:785–786.
3. Hay J B, A study of the in vitro metabolism of Androgens by Human Scalp and Pubic Skin, British Journal of Dermatology 1997; 97; 237–246.
4. Joklik W K, Willet H P, Amos D B eds. Zinsser Microbiology. 17th ed. New York: Appleton—Century—Crofts; 1980:308.
5. Nathan P A, Bernstein J A, Bielory L, et al, zafirlukast improves asthma symptoms and quality of life in patients with moderate reversible airflow obstruction J Allergy Clin Immunol. 1998;102, (6): 935–942.
6. Physicians Desk Reference, Montvale N.J.; Medical Economics Co., Inc.; 2000; 1874–1876.
7. Price, V. H., Testosterone Metabolism in the Skin. Archives Dermatology November 1975; 111; 1496–1502.

8. Quan M. Acne Vulgaris: The Old and the New. Family Practice Recertification. 1999; 21 (10):15–29.
9. Roquet, A, Dahlen, B., Kumlin, M., Ihre, E., Anstren, G., Binks, S., and Dahlen, S. Combined Antagonism of Leukotrienes and Histamine Produces Predominant Inhibition of Allergen-Induced Early and Late Phase Airway Obstruction in Asthmatics. Am J Respir. Critc. Care Med. Vol. 155. pp. 1856–1863, 1997.
10. Russel J J. Topical Therapy for Acne. AM Family Physician. 2000, 61:357–366.
11. Sheftell F D, Rapoport A M, Walker B, et al., Leukotriene Antagonist in the Prophylaxis of Migraine: A potential role for a new class of agents. Headache 1999; 39 (5): 381 Abs.
12. Spector S, Tan P A. Antileukotrienes in Chronic Urticaria Journal of Allergy and Clinical Immunology 1998; 101 (4) Part 1:572.
13. Stewart W D, Danto J L, Maddin S eds. Dermatology. Diagnosis and Treatment of Cutaneous Disorders. 4th ed. St. Louis, Mo.: The C.V. Mosby Company; 1978: 77–89.
14. Vides E A, Cabrera A, Ahem K P, et al, Effect of zafirlukast on Leprosy Reactions. International Journal of Leprosy and other Mycobacterial Diseases. 1999, 67 (1): 71–75.

What is claimed is:

1. A method of treating hair loss disorders, comprising administering to a subject in need of such treatment a therapeutically effective amount of a leukotriene receptor antagonist wherein said leukotriene D4 receptor antagonist is selected from the group consisting of zafirlukast and montelukast.

2. The method of claim 1, wherein said leukotriene receptor antagonist competitively inhibits the binding of leukotriene D4 at the leukotriene D4 receptor site.

3. The method of claim 1, wherein said leukotriene receptor antagonist is zafirlukast.

4. The method of claim 1, wherein the administration occurs at least twice per day.

5. The method of claim 1, wherein the treatment lasts at least two months.

6. The method of claim 1, wherein there is substantially no interruption in treatment.

7. The method of claim 1, wherein said hair loss disorders is selected from the group consisting of androgenic alopecia and hereditary balding.

8. The method of treating hair loss disorders of claim 1, wherein the leukotriene receptor antagonist is a $CysLT_1$-antagonist.

* * * * *